United States Patent [19]

Kikuchi et al.

[11] Patent Number: 5,827,698
[45] Date of Patent: Oct. 27, 1998

[54] LYSINE DECARBOXYLASE GENE AND METHOD OF PRODUCING L-LYSINE

[75] Inventors: Yoshimi Kikuchi; Tomoko Suzuki; Hiroyuki Kojima, all of Kawasaki, Japan

[73] Assignee: Ajinomoto Co., Inc., Tokyo, Japan

[21] Appl. No.: 849,212

[22] PCT Filed: Dec. 5, 1995

[86] PCT No.: PCT/JP95/02481

§ 371 Date: Jun. 9, 1997

§ 102(e) Date: Jun. 9, 1997

[87] PCT Pub. No.: WO96/17930

PCT Pub. Date: Jun. 13, 1996

[30] Foreign Application Priority Data

Dec. 9, 1994 [JP] Japan .................................. 6-306386

[51] Int. Cl.$^6$ .......................... C12P 13/08; C07H 21/00; C07H 21/02; C07H 21/04
[52] U.S. Cl. ......................... 435/115; 530/350; 435/71.1; 435/29; 435/183; 435/252.8; 536/23.1; 536/23.2
[58] Field of Search ............................ 530/350; 435/71.1, 435/29, 183, 252.8, 115; 536/23.2, 23.1

[56] References Cited

PUBLICATIONS

CA 111:209849. 1989.
CA 1056:36506. 1986.
Meng et al., J. Bacteriology vol. 174 p. 2659. 1992.

*Primary Examiner*—Sheela Huff
*Attorney, Agent, or Firm*—Oblon, Spivak, McClelland, Maier & Neustadt, P.C.

[57] ABSTRACT

L-lysine is produced efficiently by cultivating, in a liquid medium, a microorganism belonging to the genus Escherichia with decreased or disappeared lysine decarboxylase activity relevant to decomposition of L-lysine, for example, a bacterium belonging to the genus Escherichia with restrained expression of a novel gene coding for lysine decarboxylase and/or a known gene cadA to allow L-lysine to be produced and accumulated in a culture liquid, and collecting it.

22 Claims, 3 Drawing Sheets

LYSINE DECARBOXYLASE GENE AND METHOD OF PRODUCING L-LYSINE

TECHNICAL FIELD

The present invention relates to a novel lysine decarboxylase gene of *Escherichia coli* relevant to decomposition of L-lysine, a microorganism belonging to the genus Escherichia with restrained expression of the gene and/or another lysine decarboxylase gene known as cadA gene, and a method of producing L-lysine by using the microorganism. Recently, the demand of L-lysine as a feed additive actively increases.

BACKGROUND ART

Lysine decarboxylase, which catalyzes a reaction to produce cadaverine by decarboxylation of L-lysine, is known as an L-lysine-decomposing enzyme of *Escherichia coli*. A nucleotide sequence of its gene called cadA, and an amino acid sequence encoded by the gene have been already reported (Meng, S. and Bennett, G. N. , *J. Bacteriol.*, 174, 2659 (1992)). There are two reports for lysine decarboxylase encoded by a gene other than cadA of *Escherichia coli*, which describe that faint activity was detected in a mutant strain of *Escherichia coli* (Goldemberg, S. H. ,*J. Bacteriol.*, 141, 1428 (1980); Wertheimer, S. J. and Leifer, Z., *Biochem. Biophys. Res. Commun.*, 114, 882 (1983)). However, it was reported for this activity by Goldemberg, S. H. that the enzyme activity decreased in a degree of about 30% after a heat treatment at 60° C. for 4 minutes, while it was reported by Wertheimer, S. J. et al that no such phenomenon was observed. Accordingly, the presence of the second lysine decarboxylase is indefinite.

On the other hand, L-lysine is produced by known methods for using *Escherichia coli*, including a method comprising cultivating a mutant strain resistant to lysine analog or a recombinant strain harboring a vector with incorporated deoxyribonucleic acid which carries genetic information relevant to L-lysine biosynthesis (Japanese Patent Laid-open No. 56-18596). However, there is no report at all for L-lysine production by using a microorganism belonging to the genus Escherichia with restrained expression of the lysine decarboxylase gene.

DISCLOSURE OF THE INVENTION

An object of the present invention is to obtain a novel lysine decarboxylase gene of *Escherichia coli*, create an L-lysine-producing microorganism belonging to the genus Escherichia with restrained expression of the gene and/or the cadA gene, and provide a method of producing L-lysine by cultivating the microorganism belonging to the genus Escherichia. When the present inventors created an *Escherichia coli* strain in which the cadA gene as a known lysine decarboxylase gene was destroyed, it was found that cadaverine as a decomposition product of L-lysine by lysine decarboxylase was still produced in this microbial strain. Thus the present inventors assumed that a novel lysine decarboxylase gene should be present in *Escherichia coli*, and it might greatly affect fermentative production of L-lysine by using a microorganism belonging to the genus Escherichia. As a result of trials to achieve cloning of the gene, the present inventors succeeded in obtaining a novel lysine decarboxylase gene different from the cadA gene. It was also found that the L-lysine-decomposing activity was remarkably decreased or disappeared, and the L-lysine productivity was significantly improved by restraining expression of this gene, and restraining expression of the cadA gene in an L-lysine-producing microorganism of *Escherichia coli*. Thus the present invention was completed.

Namely, the present invention provides a novel gene which codes for lysine decarboxylase originating from *Escherichia coli*. This gene has been designated as "ldc" gene.

In another aspect, the present invention provides a microorganism belonging to the genus Escherichia having L-lysine productivity with decreased or disappeared lysine decarboxylase activity in cells.

In still another aspect, the present invention provides a method of producing L-lysine comprising the steps of cultivating, in a liquid medium, the microorganism belonging to the genus Escherichia described above to allow L-lysine to be produced and accumulated in a culture liquid, and collecting it.

The microorganism belonging to the genus Escherichia described above includes a microorganism in which lysine decarboxylase activity in cells is decreased or disappeared by restraining expression of the ldc gene and/or the cadA gene.

The present invention will be described in detail below.

<1>Preparation of DNA fragment containing novel lysine decarboxylase gene

A DNA fragment containing the novel lysine decarboxylase gene (ldc) of the present invention can be obtained as follows from an available strain of *Escherichia coli*, for example, K-12 strain or a derivative strain therefrom.

At first, the cadA gene, which is a gene of known lysine decarboxylase, is obtained from chromosomal DNA of W3110 strain originating from *Escherichia coli* K-12 by using a polymerase chain reaction method (hereinafter referred to as "PCR method"). The nucleotide sequence of the cadA gene, and the amino acid sequence encoded by it are shown in SEQ ID NOS:5 and 6 respectively. DNA fragments having sequences similar to the cadA gene are cloned from a chromosomal DNA library of *Escherichia coli* W3110 in accordance with a method for using a plasmid vector or a phage vector to confirm whether or not the novel lysine decarboxylase gene is contained in the DNA fragments. The confirmation of the fact that the objective gene is contained can be performed in accordance with a Southern hybridization method by using a probe prepared by the PCR method.

A nucleotide sequence of the gene contained in the DNA fragment thus obtained is determined as follows. At first, the DNA fragment is ligated with a plasmid vector autonomously replicable in cells of *Escherichia coli* to prepare recombinant DNA which is introduced into competent cells of *Escherichia coli*. An obtained transformant is cultivated in a liquid medium, and the recombinant DNA is recovered from proliferated cells. An entire nucleotide sequence of the DNA fragment contained in the recovered recombinant DNA is determined in accordance with a dideoxy method (Sanger, F. et al., *Proc. Natl. Acad. Sci.*, 74, 5463 (1977)). The structure of DNA is analyzed to determine existing positions of promoter, operator, SD sequence, initiation codon, termination codon, open reading frame, and so on.

The novel lysine decarboxylase gene of the present invention has a sequence from 1005–1007th ATG to 3141–3143rd GGA of the entire nucleotide sequence of the DNA fragment shown in SEQ ID NO:3 in Sequence Listing. This gene codes for lysine decarboxylase having an amino acid sequence shown in SEQ ID NO:4 in Sequence Listing. It has been found that the homology between the novel lysine decaroboxylase and the lysine decaroboxylase coded by cadA gene is 69.4%.

The gene of the present invention may be those which code for lysine decarboxylase having the amino acid sequence shown in SEQ ID NO:4 in Sequence Listing, a nucleotide sequence of which is not limited to the nucleotide sequence described above. The lysine decarboxylase encoded by the gene of the present invention may have substitution, deletion, or insertion of one or a plurality of amino acid residues without substantial deterioration of the lysine decarboxylase activity, in the amino acid sequence described above. Genes which code for lysine decarboxylase having such deletion, insertion, or substitution can be obtained from variants, spontaneous mutant strains, or artificial mutant strains of *Escherichia coli*, or from microorganisms belonging to the genus Escherichia other than *Escherichia coli*. The mutant genes which code for lysine decarboxylase having deletion, insertion, or substitution can be also obtained by performing an in vitro mutation treatment or a site-directed mutagenesis treatment for the gene which codes for lysine decarboxylase having the amino acid sequence shown in SEQ ID NO:4. These mutation treatments can be performed in accordance with methods well-known to those skilled in the art as described below.

However, the gene, which codes for lysine decarboxylase having substitution, deletion, or insertion of one or a plurality of amino acid residues as referred to herein, includes those which originate from the "ldc gene" and can be regarded to be substantially the same as the ldc gene. It is not intended to extend the meaning to those genes having different origins. It is impossible to concretely prescribe a certain range of the "plurality". However, it will be readily understood by those skilled in the art that, for example, the cadA gene which codes for the protein different in not less than 200 amino acid residues from one having the amino acid sequence shown in SEQ ID NO:3 is different from the gene of the present invention, and the genes which code for proteins having equivalent lysine decarboxylase activity are included in the present invention even if they are different from one having the amino acid sequence shown in SEQ ID NO:3 with respect to two or three amino acid residues.

<2>Creation of microorganism belonging to the genus Escherichia with restrained expression of lysine decarboxylase gene The microorganism belonging to the genus Escherichia of the present invention is a microorganism belonging to the genus Escherichia in which the lysine decarboxylase activity in cells is decreased or disappeared. The microorganism belonging to the genus Escherichia includes *Escherichia coli*. The lysine decarboxylase activity in cells is decreased or disappeared, for example, by restraining expression of any one of or both of the novel lysine decarboxylase gene (ldc) and the known cadA gene described above. Alternatively, the lysine decarboxylase activity in cells can be also decreased or disappeared by decreasing or disappearing the specific activities of lysine decarboxylase enzymes encoded by these genes, by modifying the structure of the enzymes.

The means for restraining expression of the ldc gene and the known cadA gene includes, for example, a method for restraining expression of the genes at a transcription level by causing substitution, deletion, insertion, addition, or inversion of one or a plurality of nucleotides in promoter sequences of these genes, and decreasing promoter activities (M. Rosenberg and D. Court, *Ann. Rev. Genetics* 13 (1979) p.319, and P. Youderian, S. Bouvier and M. Susskind, Cell 30 (1982) p.843–853). Alternatively, the expression of these genes can be restrained at a translation level by causing substitution, deletion, insertion, addition, or inversion of one or a plurality of nucleotides in a region between an SD sequence and an initiation codon (J. J. Dunn, E. Buzash-Pollert and F. W. Studier, *Proc. Nat. Acad. Sci. U.S.A.*, 75 (1978) p.2743). In addition, in order to decrease or disappear the specific activity of the lysine decarboxylase enzyme, a method is available, in which the coding region of the lysine decarboxylase gene is modified or destroyed by causing substitution, deletion, insertion, addition, or inversion of one or a plurality of nucleotides in a nucleotide sequence in the coding region.

The gene, on which nucleotide substitution, deletion, insertion, addition, or inversion is allowed to occur, may be ldc genes or cadA genes having substitution, deletion, or insertion of one or a plurality of amino acid residues which do not deteriorate the substantial activity of encoded lysine decarboxylase, in addition to the ldc gene or the cadA gene.

The method to cause nucleotide substitution, deletion insertion, addition, or inversion in the gene specifically includes a site-directed mutagenesis method (Kramer, W. and Frits, H. J. , *Mothods in Enzymoloay*, 154, 350 (1987)), and a treatment method by using a chemical agent such as sodium hyposulfite and hydroxylamine (Shortle, D. and Nathans, D. , *Proc. Natl. Acad. Sci. U.S.A.*, 75, 270 (1978)).

The site-directed mutagenesis method is a method to use a synthetic oligonucleotide, which is a technique to enable introduction of optional substitution, deletion, insertion, addition, or inversion into an optional and limited nucleotide pair. In order to utilize this method, at first, a single strand is prepared by denaturing a plasmid having a cloned objective gene with a determined nucleotide sequence of DNA. Next, a synthetic oligonucleotide complementary to a portion intended to cause mutation is synthesized. However, in this procedure, the synthetic oligonucleotide is not allowed to have a completely complementary sequence, but it is designed to have optional nucleotide substitution, deletion, insertion, addition, or inversion. After that, the single strand DNA is annealed with the synthetic oligonucleotide having the optional nucleotide substitution, deletion, insertion, addition, or inversion. A complete double strand plasmid is synthesized by using T4 ligase and Klenow fragment of DNA polymerase I, which is introduced into competent cells of *Escherichia coli*. Some of transformants thus obtained have a plasmid containing a gene in which the optional nucleotide substitution, deletion, insertion, addition, or inversion is fixed. A recombinant PCR method (*PCR Technology*, Stockton press (1989)) may be mentioned as a similar method capable of introducing mutation into a gene to make modification or destruction.

The method to use the chemical agent is a method in which mutation having nucleotide substitution, deletion, insertion, addition, or inversion is randomly introduced into a DNA fragment by treating the DNA fragment containing an objective gene directly with sodium hyposulfite, hydroxylamine or the like.

Expression of the ldc gene and/or the cadA gene in cells can be restrained by substituting a normal gene on chromosome of a microorganism belonging to the genus Escherichia with the modified or destroyed gene obtained by the introduction of mutation as described above. The method for substituting the gene includes methods which utilize homologous recombination (*Experiments in Molecular Genetics*, Cold Spring Harbor Laboratory press (1972); Matsuyama, S. and Mizushima, S. , *J. Bacteriol.*, 162, 1196

(1985)). The homologous recombination is based on an ability generally possessed by the microorganism belonging to the genus Escherichia. When a plasmid or the like having homology to a sequence on chromosome is introduced into cells, recombination occurs at a certain frequency at a place of the sequence having the homology, and the whole of the introduced plasmid is incorporated on the chromosome. After that, if further recombination occurs at the place of the sequence having the homology on the chromosome, the plasmid falls off from the chromosome again. However, during this process, the gene with introduced mutation is occasionally fixed preferentially on the chromosome depending on the position at which recombination takes place, and an original normal gene falls off from the chromosome together with the plasmid. Selection of such microbial strains makes it possible to obtain a microbial strain in which the normal gene on the chromosome is substituted with the modified or destroyed gene obtained by the introduction of mutation having nucleotide substitution, deletion, insertion, addition, or inversion.

The microorganism belonging to the genus Escherichia to be subjected to the gene substitution is a microorganism having L-lysine productivity. The microorganism belonging to the genus Escherichia having L-lysine productivity, for example, a microbial strain of *Escherichia coli* can be obtained by applying a mutation treatment to a strain having no L-lysine productivity to give it resistance to a lysine analog such as S-(2-aminoethyl)-L-cysteine (hereinafter referred to as "AEC"). Methods for the mutation treatment include methods in which cells of *Escherichia coli* are subjected to a treatment with a chemical agent such as N-methyl-N'-nitro-N-nitrosoguanidine and nitrous acid, or a treatment with irradiation of ultraviolet light, radiation or the like. Such a microbial strain specifically includes *Escherichia coli* AJ13069 (FERM P-14690). This microbial strain was bred by giving AEC resistance to W3110 strain originating from *Escherichia coli* K-12. *Escherichia coli* AJ13069 was deposited in National Institute of Bioscience and Human Technology of Agency of Industrial Science and Technology (postal code:305, 1–3, Higashi 1-chome, Tsukuba-shi, Ibaraki-ken, Japan) under an accession number of FERM P-14690 on Dec. 6, 1994, transferred to international deposition based on the Budapest Treaty on Sep. 29, 1995, and given an accession number of FERM BP-5252.

The microbial strain of *Escherichia coli* having L-lysine productivity can be also bred by introducing and enhancing DNA which carries genetic information relevant to L-lysine biosynthesis by means of the gene recombination technology. The gene to be introduced are genes which code for enzymes on the biosynthetic pathway of L-lysine, such as aspartokinase, dihydrodipicolinate synthetase, dihydrodipicolinate reductase, succinyldiaminopimelate transaminase, and succinyldiaminopimelate deacylase. In the case of a gene of the enzyme which undergoes feedback inhibition by L-lysine such as aspartokinase and dihydrodipicolinate synthetase, it is desirable to use a mutant type gene coding for an enzyme which is desensitized from such inhibition. In order to introduce and enhance the gene, a method is available, in which the gene is ligated with a vector autonomously replicable in cells of *Escherichia coli* to prepare recombinant DNA with which *Escherichia coli* is transformed. Alternatively, the gene can be also incorporated into chromosome of a host in accordance with a method to use transduction, transposon (Berg, D. E. and Berg, C. M. , *Bio/Technol.*, 1, 417 (1983)), Mu phage (Japanese Patent Laid-open No. 2-109985), or homologous recombination (*Experiments in Molecular Genetics*, Cold Spring Harbor Lab. (1972)).

Other methods to obtain the microorganism belonging to the genus Escherichia with destroyed function of the gene include a method to cause genetic mutation by applying a treatment with a chemical agent such as N-methyl-N'-nitro-N-nitrosoguanidine and nitrous acid, or a treatment with irradiation of ultraviolet light, radiation or the like, to cells of the microorganism belonging to the genus Escherichia having the gene.

In Example described below, an *Escherichia coli* strain with destroyed function of the lysine decarboxylase gene was created by deleting a part of its coding region, and inserting a drug resistance gene instead of it to obtain a lysine decarboxylase gene which was used to substitute a lysine decarboxylase gene on chromosome of *Escherichia coli* in accordance with the method utilizing homologous recombination described above.

It is possible to restrain expression of any one of the novel lysine decarboxylase gene of the present invention and cadA gene, or restrain expression of both of them, in one microbial strain. Expression of the lysine decarboxylase gene may be restrained in the microorganism belonging to the genus Escherichia having L-lysine productivity, or L-lysine productivity may be given to the microorganism belonging to the genus Escherichia with restrained expression of the lysine decarboxylase gene in accordance with the method described above.

<3>Production of L-lysine by using microorganism belonging to the genus Escherichia with restrained expression of lysine decarboxylase gene A considerable amount of L-lysine is produced and accumulated in a culture liquid by cultivating the microorganism belonging to the genus Escherichia with restrained expression of the lysine decarboxylase gene obtained as described above. The accumulation amount of L-lysine is increased only by restraining expression of the known cadA gene. However, it is more effective for increasing the accumulation amount of L-lysine to restrain expression of the novel lysine decarboxylase gene of the present invention. The most preferable result for L-lysine production is obtained by using a microbial strain in which expression of both of the cadA gene and the novel gene of the present invention is restrained.

The medium to be used for L-lysine production is an ordinary medium containing a carbon source, a nitrogen source, inorganic ions, and optionally other organic trace nutrient sources. As the carbon source, it is possible to use sugars such as glucose, lactose, galactose, fructose, and starch hydrolysate; alcohols such as glycerol and sorbitol; and organic acids such as fumaric acid, citric acid, and succinic acid. As the nitrogen source, it is possible to use inorganic ammonium salts such as ammonium sulfate, ammonium chloride, and ammonium phosphate; organic nitrogen sources such as soybean hydrolysate; ammonia gas; and aqueous ammonia. As the inorganic ions, potassium phosphate, magnesium sulfate, iron ion, manganese ion and so on are added in small amounts. Other than the above, it is desirable to contain vitamin $B_1$, yeast extract or the like in appropriate amounts as the organic trace nutrient sources.

Cultivation is preferably carried out under an aerobic condition for about 16–72 hours. The cultivation temperature is controlled at 30° C. to 45° C., and pH is controlled at 5–7 during cultivation. Inorganic or organic, acidic or alkaline substances, or ammonia gas or the like can be used for pH adjustment.

After completion of the cultivation, collection of L-lysine from a fermented liquor can be appropriately carried out by combining an ordinary ion exchange resin method, a precipitation method, and other known methods.

BEST MODE FOR CARRYING OUT THE INVENTION

The present invention will be more specifically explained below with reference to Examples.

EXAMPLE 1

(1) Cloning of novel lysine decarboxylase gene

Chromosomal DNA was extracted in accordance with an ordinary method from cells of W3110 strain of *Escherichia coli* K-12 obtained from National Institute of Genetics (Yata 1111, Mishima-shi, Shizuoka-ken, Japan). On the other hand, two synthetic DNA primers as shown in SEQ ID NOS:1 and 2 in Sequence Listing were synthesized in accordance with an ordinary method on the basis of the nucleotide sequence of the cadA gene (see SEQ ID NO:5) described in Meng, S. and Bennett, G. N. ,*J. Bacteriol.,* 174, 2659 (1992). They had sequences homologous to a 5'-terminal upstream portion and a 3'-terminal portion of the cadA gene respectively. The chromosomal DNA and the DNA primers were used to perform a PCR method in accordance with the method of Erlich et al. (*PCR Technology*, Stockton press (1989)). Thus a DNA fragment of 2.1 kbp containing almost all parts of the cadA gene was obtained. This fragment was labeled with Random Primer Labeling Kit (produced by Takara Shuzo) and [α-$^{32}$P]dCTP (produced by Amersham Japan) to prepare a probe for hybridization.

Next, hybridization was performed in accordance with an ordinary method (*Molecular Cloning* (2nd edition), Cold Spring Harbor Laboratory press (1989)) by using the prepared probe and *Escherichia coli*/Gene Mapping Membrane (produced by Takara Shuzo). A library of Kohara et al. (lambda phage library of *Escherichia coli* chromosomal DNA:see Kohara, Y. et al. *Cell,* 50, 495–508 (1987)) had been adsorbed to *Escherichia coli*/Gene Mapping Membrane. Lambda phage clones having sequences similar to the cadA gene were screened by weakening the condition for washing the probe (2×SSC, 55° C., 30 minutes), when the hybridization was performed. As a result, we succeeded in finding weak signals from three clones of E2B8, 6F5H, and 10F9, in addition to strong signals from clones containing the cadA gene region (21H11, 5G7). Insertion sequences of the three lambda phage clones of E2B8, 6F5H, and 10F9 continue on chromosome of *Escherichia coli* while overlapping with each other. Thus lambda phage DNA of 6F5H belonging to the library of Kohara et al. (Kohara, Y. et al. *Cell,* 50, 495–508 (1987)) was separated in accordance with an ordinary method, which was digested with various restriction enzymes to perform Southern blot hybridization by using the probe described above in accordance with a method similar to one described above. As a result, it was revealed that a sequence similar to the cadA gene was present in a DNA fragment of about 5 kbp obtained by digestion with HindIII.

Figure 1:
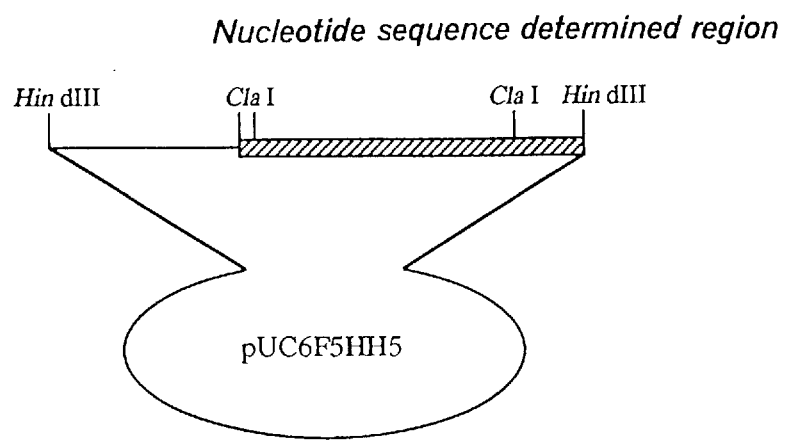
FIG. 1 shows a structure of a plasmid pUC6F5HH5 containing the novel lysine decarboxylase gene.

Thus, the fragment of about 5 kbp obtained by digesting the lambda phage DNA of 6F5H with HindIII was ligated with a HindIII digest of a plasmid pUC19 (produced by Takara Shuzo) by using T4 DNA ligase. This reaction mixture was used to transform *Escherichia coli* JM109 (produced by Takara Shuzo) to obtain ampicillin-resistant strains grown on a complete plate medium (containing 10 g of polypeptone, 5 g of yeast extract, and 5 g of sodium chloride in 1 L of water) added with 50 mg/mL ampicillin. A microbial strain was obtained therefrom, which harbored a plasmid with insertion of the fragment of about 5 kbp obtained by digesting the lambda phage DNA of 6F5H with HindIII. A plasmid was extracted from cells thereof, and a plasmid pUC6F5HH5 was obtained. FIG. 1 shows a structure of the plasmid pUC6F5HH5.

*Escherichia coli* JM109/pUC6F5HH5 harboring this plasmid was designated as AJ13068, deposited in National Institute of Bioscience and Human Technology of Agency of Industrial Science and Technology under an accession number of FERM P-14689 on Dec. 6, 1994, transferred to international deposition based on the Budapest Treaty on Sep. 29, 1995, and given an accession number of FERM BP-5251.

(2) Determination of nucleotide sequence of novel lysine decarboxylase gene

A nucleotide sequence of a region between restriction enzyme sites of ClaI and HindIII of obtained pUC6F5HH5 was determined in accordance with a method described in *Molecular Cloning* (2nd edition), Cold Spring Harbor Laboratory press (1989). As a result, it was revealed that the nucleotide sequence shown in SEQ ID NO:3 in Sequence Listing was encoded. This DNA sequence contains an open reading frame which codes for the amino acid sequence shown in SEQ ID NO:4 in Sequence Listing.

(3) Preparation of *Escherichia coli* having L-lysine productivity

*Escherichia coli* W3110 was cultivated at 37° C. for 4 hours in a complete medium (containing 10 g of polypeptone, 5 g of yeast extract, and 5 g of sodium chloride in 1 L of water) to obtain microbial cells which were subjected to a mutation treatment at 37° C. for 30 minutes in a solution of N-methyl-N'-nitro-N-nitrosoguanidine at a concentration of 200 μg/ml, washed, and then applied to a minimum plate medium (containing 7 g of disodium hydrogenphosphate, 3 g of potassium dihydrogenphosphate, 1 g of ammonium chloride, 0.5 g of sodium chloride, 5 g of glucose, 0.25 g of magnesium sulfate hepta-hydrate, and 15 g of agar in 1 L of water) added with 5 g/L of AEC. AEC-resistant strains were obtained by separating colonies appeared after cultivation at 37° C. for 48 hours. WC196 strain as one strain among them had L-lysine productivity. WC196 strain was designated as AJ13069, deposited in National Institute of Bioscience and Human Technology of Agency of Industrial Science and Technology under an accession number of FERM P-14690 on Dec. 6, 1994, transferred to international deposition based on the Budapest Treaty on Sep. 29, 1995, and given an accession number of FERM BP-5252.

Figure 2:
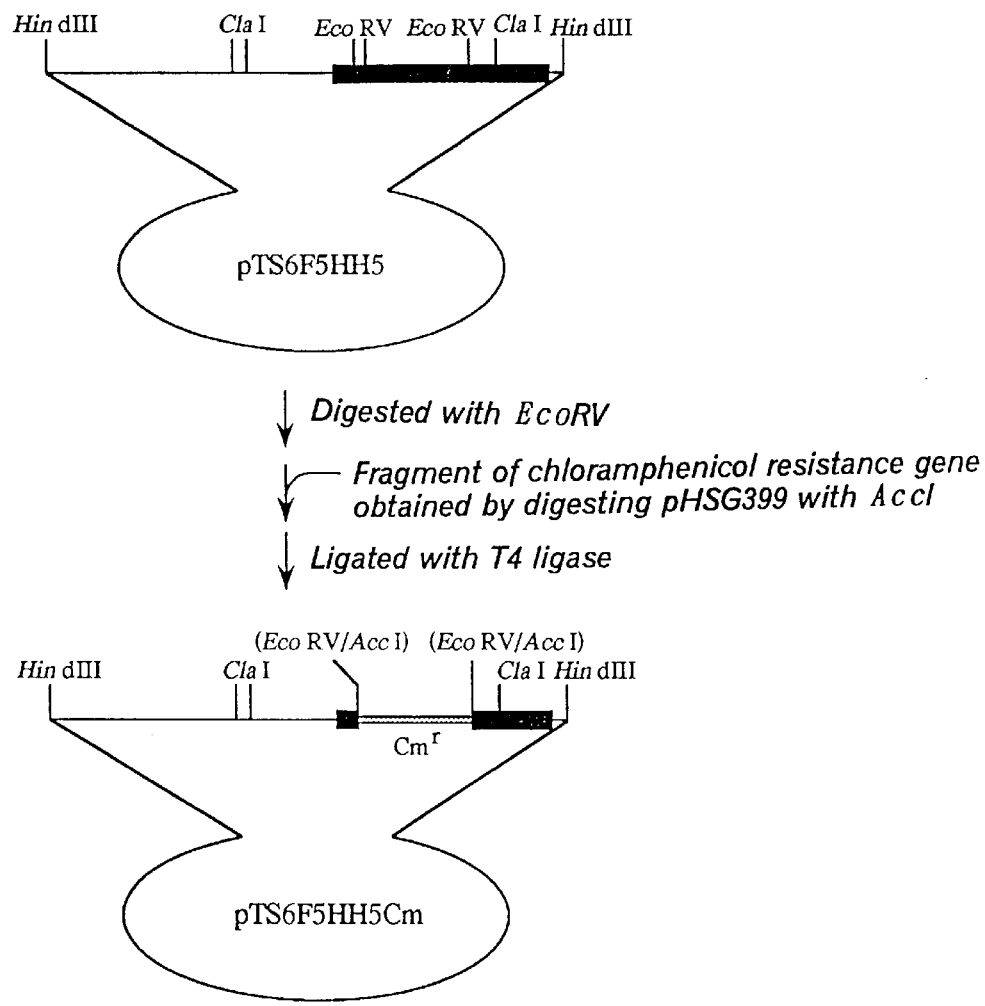
FIG. 2 shows a structure of a temperature-sensitive plasmid pTS6F5HH5 containing the novel lysine decarboxylase gene, and construction of a plasmid pTS6F5HH5Cm in which a part of the gene is substituted with a fragment containing a chloramphenicol resistance gene.

(4) Creation of WC196 strain with destroyed function of novel lysine decarboxylase gene The fragment of about 5 kbp obtained by digesting the lambda phage DNA of 6F5H with HindIII described above was ligated with a HindIII digest of a temperature-sensitive plasmid pMAN031 (Yasueda, H. et al., *Appl. Microbiol. Biotechnol.*, 36, 211 (1991)) by using T4 DNA ligase. This reaction mixture was used to transform *Escherichia coli* JM109, followed by cultivation at 37° C. for 24 hours on a complete plate medium added with 50 mg/L of ampicillin to grow ampicillin-resistant strains. A microbial strain was obtained therefrom, which harbored a plasmid with insertion of the fragment of about 5 kbp obtained by digesting the lambda phage DNA of 6F5H with HindIII. A plasmid was extracted from cells of this strain, and a plasmid pTS6F5HH5 was obtained. The plasmid pTS6F5HH5 was digested with EcoRV to remove a DNA fragment of about 1 kbp. Next, T4 ligase was used to insert a fragment having a chloramphenicol resistance gene of about 1 kbp obtained by digesting pHSG399 (produced by Takara Shuzo) with AccI. Thus a plasmid pTS6F5HH5Cm was constructed. As a result of the operation described above, we succeeded in construction of the plasmid having a DNA fragment with destroyed function of the novel lysine decarboxylase gene. FIG. 2 shows a structure of the plasmid pTS6F5HH5, and the plasmid pTS6F5HH5Cm.

Next, a strain was created, in which the novel lysine decarboxylase gene on chromosome of WC196 strain was substituted with the DNA fragment with destroyed function of the novel lysine decarboxylase gene, in accordance with a general homologous recombination technique (Matsuyama, S. and Mizushima, S., *J. Bacteriol.*, 162, 1196 (1985)) by utilizing the property of temperature sensitivity of the plasmid pTS6F5HH5Cm. Namely, WC196 strain was transformed with the plasmid pTS6F5HH5Cm to firstly obtain a strain which was resistant to ampicillin and resistant to chloramphenicol at 30° C. Next, this strain was used to obtain a strain which was resistant to ampicillin and resistant to chloramphenicol at 42° C. Further, this strain was used to obtain a strain which was sensitive to ampicillin and resistant to chloramphenicol at 30° C. Thus the strain as described above was created, in which the novel lysine decarboxylase gene on chromosome of WC196 strain was substituted with the DNA fragment with destroyed function of the novel lysine decarboxylase gene. This strain was designated as WC196L strain.

(5) Creation of WC196 strain and WC196L strain with deficiency of cadA gene

*Escherichia coli*, in which cadA as the known lysine decarboxylase gene is destroyed, is already known, including, for example, GNB10181 strain originating from *Escherichia coli* K-12 (see Auger, E. A. et al., *Mol. Microbiol.*, 3, 609 (1989); this microbial strain is available from, for example, *E. coli* Genetic Stock Center (Connecticut, USA)). It has been revealed that the region of the cadA gene is deficient in this microbial strain. Thus the character of cadA gene deficiency of GNB10181 strain was transduced into WC196 strain in accordance with a general method by using P1 phage (*A Short Course in Bacterial Genetics*, Cold Spring Harbor Laboratory Press (1992)) to create WC196C strain. Deficiency of the cadA gene of WC196 strain was confirmed by Southern blot hybridization. In addition, WC196LC strain with deficiency of the cadA gene was created from WC196L strain in accordance with a method similar to one described above.

EXAMPLE 2

(1) Confirmation of L-lysine-decomposing activities of WC196, WC196C, WC196L, and WC196LC strains The four created strains described above were cultivated at 37° C. for 17 hours by using a medium for L-lysine production (containing 40 g of glucose, 16 g of ammonium sulfate, 1 g of potassium dihydrogenphosphate, 2 g of yeast extract, 10 mg of manganese sulfate tetra-to penta-hydrate, and 10 mg of iron sulfate hepta-hydrate in 1 L of water; pH was adjusted to 7.0 with potassium hydroxide, and then 30 g of separately sterilized calcium carbonate was added). Recovered microbial cells were washed twice with a physiological saline solution, suspended in a medium for assaying L-lysine decomposition (containing 17 g of disodium hydrogenphosphate dodeca-hydrate, 3 g of potassium dihydrogenphosphate, 0.5 g of sodium chloride, and 10 g of L-lysine hydrochloride in 1 L of water), and cultivated at 37° C. for 31 hours.

Figure 3:
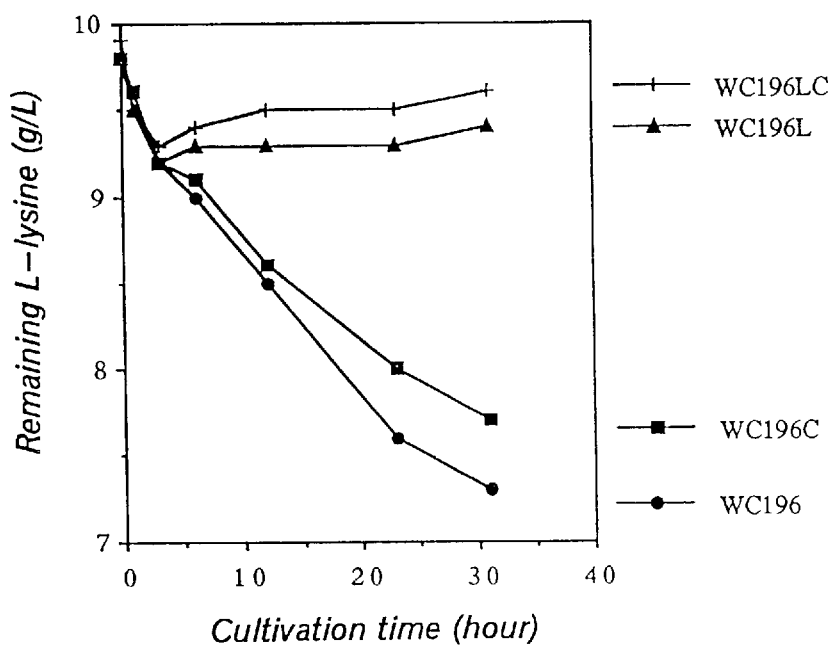
FIG. 3 shows comparison of L-lysine-decomposing activities in a strain WC196 harboring a normal lysine decarboxylase gene, and strains WC196C, WC196L, and WC196LC with destroyed lysine decarboxylase genes.

FIG. 3 shows changes in remaining L-lysine amounts in culture liquids in accordance with the passage of time. The amount of L-lysine was quantitatively determined by using Biotech Analyzer AS-210 (produced by Asahi Chemical Industry). Significant decomposition of L-lysine was observed in WC196 strain. However, the decomposing activity was decreased a little in WC196C strain with deficiency of the cadA gene as the known lysine decarboxylase gene. Decomposition of L-lysine was not observed in WC196L and WC196LC strains with destroyed function of the novel lysine decarboxylase gene. Remaining L-lysine in the culture liquid decreased during a period up to about 3 hours of cultivation in any of the microbial strains. However, this phenomenon was caused by incorporation of L-lysine into microbial cells, and not caused by decomposition.

(2) Production of L-lysine by WC196, WC196C, WC196L, and WC196LC strains

The four strains described above were cultivated at 37° C. for 20 hours in the medium for L-lysine production described above. The amounts of L-lysine and cadaverine produced and accumulated in culture liquids were measured. The amount of L-lysine was quantitatively determined by using Biotech Analyzer AS-210 as described above. The amount of cadaverine was quantitatively determined by using high performance liquid chromatography.

Results are shown in Table 1. The accumulation of L-lysine was increased, and the accumulation of cadaverine as a decomposition product of L-lysine was decreased in WC196C strain with destruction of the cadA gene as compared with WC196 strain, and in WC196L strain with destroyed function of the novel lysine decarboxylase gene as compared with WC196 and WC196C strains. The accumulation of L-lysine was further increased, and the accumulation of cadaverine as a decomposition product of L-lysine was not detected in WC196LC strain with destroyed function of the both lysine decarboxylase genes.

TABLE 1

| Microbial strain | L-lysine accumulation (g/L) | Cadaverine accumulation (g/L) |
| --- | --- | --- |
| WC196 | 1.4 | 0.6 |
| WC196C | 1.9 | 0.4 |
| WC196L | 2.3 | 0.1 |
| WC196LC | 3.3 | not detected |

EXAMPLE 3

*Escherichia coli* WC196LC with disappeared L-lysine-decomposing activity was transformed with pUC6F5HH5 containing the novel lysine decarboxylase gene to obtain an ampicillin-resistant strain. WC196LC strain and WC196LC/pUC6F5HH5 strain were cultivated at 37° C. for 16 hours in a medium for L-lysine production added with 5 g/L of L-lysine, and the amount of produced cadaverine was measured.

Results are shown in Table 2. WC196LC strain failed to convert L-lysine into cadaverine, while WC196LC/pUC6F5HH5 strain had an ability to convert L-lysine into cadaverine.

TABLE 2

| Microbial strain | Production amount of cadaverine (g/L) |
|---|---|
| WC196LC | not detected |
| WC196LC/pUC6F5HH5 | 0.93 |

Industrial Applicability

The novel lysine decarboxylase gene of the present invention participates in decomposition of L-lysine in *Escherichia coli*. L-lysine can be produced inexpensively and efficiently by cultivating the bacterium belonging to the genus Escherichia having L-lysine productivity with restrained expression of the gene described above and/or the cadA gene.

What is claimed is:

1. An isolated nucleic acid molecule encoding a lysine decarboxylase, wherein the lysine decarboxylase comprises the amino acid sequence of SEQ ID NO:4.

2. The isolated nucleic acid molecule of claim 1 comprising a sequence corresponding to position 1005 through position 3143 of SEQ ID NO:3.

3. An isolated microorganism belonging to the genus Escherichia,
   wherein the microorganism contains a mutant of a wild-type gene encoding a wild-type lysine decarboxylase;
   the microorganism lacks the wild-type gene encoding the wild-type lysine decarboxylase;
   the wild-type lysine decarboxylase comprises the amino acid sequence of SEQ ID NO:4; and
   the mutant gene encodes no lysine decarboxylase having decarboxylating activity, the mutant gene encodes a mutant lysine decarboxylase having less decarboxylating activity than the wild-type lysine decarboxylase, or the mutant gene contains a mutation in a regulatory region causing the microorganism to produce less of the wild-type lysine decarboxylase than a microorganism containing the wild-type gene encoding the wild-type lysine decarboxylase.

4. The isolated microorganism of claim 3, wherein the mutant gene contains a mutation in a regulatory region causing the microorganism to produce less of the wild-type lysine decarboxylase than a microorganism containing the wild-type gene encoding the wild-type lysine decarboxylase.

5. The isolated microorganism of claim 3 belonging to the species *Escherichia coli*.

6. The isolated microorganism of claim 3, wherein the wild-type gene comprises a sequence corresponding to position 1005 through position 3143 of SEQ ID NO:3.

7. The isolated microorganism of claim 3, wherein the mutant gene encodes no lysine decarboxylase having decarboxylating activity.

8. The isolated microorganism of claim 3, wherein the mutant gene encodes a mutant lysine decarboxylase having less decarboxylating activity than the wild-type lysine decarboxylase.

9. The isolated microorganism of claim 3,
   wherein the microorganism further contains a second mutant of a second wild-type gene encoding a second wild-type lysine decarboxylase;
   the microorganism lacks the second wild-type gene encoding the second wild-type lysine decarboxylase;
   the second wild-type lysine decarboxylase comprises the amino acid sequence of SEQ ID NO:6; and
   the second mutant gene encodes no lysine decarboxylase having decarboxylating activity, the second mutant gene encodes a second mutant lysine decarboxylase having less decarboxylating activity than the second wild-type lysine decarboxylase, or the second mutant gene contains a mutation in a regulatory region causing the microorganism to produce less of the second wild-type lysine decarboxylase than a microorganism containing the second wild-type gene encoding the second wild-type lysine decarboxylase.

10. The isolated microorganism of claim 9, wherein the second mutant gene contains a mutation in a regulatory region causing the microorganism to produce less of the second wild-type lysine decarboxylase than a microorganism containing the second wild-type gene encoding the second wild-type lysine decarboxylase.

11. The isolated microorganism of claim 9, wherein the second mutant gene encodes no lysine decarboxylase having decarboxylating activity.

12. The isolated microorganism of claim 9, wherein the second mutant gene encodes a second mutant lysine decarboxylase having less decarboxylating activity than the second wild-type lysine decarboxylase.

13. A method for producing L-lysine, comprising:
   (a) cultivating the microorganism of claim 3 in a liquid medium, thereby producing the L-lysine and accumulating the L-lysine in the liquid medium, and
   (b) collecting the L-lysine produced and accumulated in step (a).

14. The method of claim 13, wherein the mutant gene contains a mutation in a regulatory region causing the microorganism to produce less of the wild-type lysine decarboxylase than a microorganism containing the wild-type gene encoding the wild-type lysine decarboxylase.

15. The method of claim 13, wherein the microorganism belongs to the species *Escherichia coli*.

16. The method of claim 13, wherein the wild-type gene comprises a sequence corresponding to position 1005 through position 3143 of SEQ ID NO:3.

17. The method of claim 13, wherein the mutant gene encodes no lysine decarboxylase having decarboxylating activity.

18. The method of claim 13, wherein the mutant gene encodes a mutant lysine decarboxylase having less decarboxylating activity than the wild-type lysine decarboxylase.

19. The method of claim 13,
   wherein the microorganism further contains a second mutant gene of a second wild-type gene encoding a second wild-type lysine decarboxylase;
   the microorganism lacks the second wild-type gene encoding the second wild-type lysine decarboxylase;
   the second wild-type lysine decarboxylase comprises the amino acid sequence of SEQ ID NO:6; and the second mutant gene encodes no lysine decarboxylase having decarboxylating activity, the second mutant gene encodes a second mutant lysine decarboxylase having less decarboxylating activity than the second wild-type lysine decarboxylase, or the second mutant gene contains a mutation in a regulatory region causing the microorganism to produce less of the second wild-type lysine decarboxylase than a microorganism containing the second wild-type gene encoding the second wild-type lysine decarboxylase.

20. The method of claim 19, wherein the second mutant gene contains a mutation in a regulatory region causing the microorganism to produce less of the second wild-type lysine decarboxylase than a microorganism containing the second wild-type gene encoding the second wild-type lysine decarboxylase.

21. The method of claim 19, wherein the second mutant gene encodes no lysine decarboxylase having decarboxylating activity.

22. The method of claim 19, wherein the second mutant gene encodes a second mutant lysine decarboxylase having less decarboxylating activity than the second wild-type lysine decarboxylase.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( i i i ) HYPOTHETICAL: NO ( i v ) ANTI-SENSE: NO ( x i ) SEQUENCE DESCRIPTION: SEQ ID NO:1:

TGGATAACCA CACCGCGTCT    20

( 2 ) INFORMATION FOR SEQ ID NO:2:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( i i i ) HYPOTHETICAL: NO ( i v ) ANTI-SENSE: YES ( x i ) SEQUENCE DESCRIPTION: SEQ ID NO:2:

GGAAGGATCA TATTGGCGTT    20

( 2 ) INFORMATION FOR SEQ ID NO:3:

( i ) SEQUENCE CHARACTERISTICS:
( A ) LENGTH: 3183 base pairs
( B ) TYPE: nucleic acid
( C ) STRANDEDNESS: double
( D ) TOPOLOGY: linear ( i i ) MOLECULE TYPE: DNA (genomic)

-continued (iii) HYPOTHETICAL: NO (iv) ANTI-SENSE: NO (vi) ORIGINAL SOURCE:
   (A) ORGANISM: Escherichia Coli
   (B) STRAIN: W3110

(ix) FEATURE:
   (A) NAME/KEY: CDS
   (B) LOCATION: 1005..3143

(xi) SEQUENCE DESCRIPTION: SEQ ID NO:3:

```
ATCGATTCTC TGACTGCGGT TAGCCGTCAG GATGAGAAAC TGGATATTAA CATCGATGAA      60

GAAGTGCATC GTCTGCGTGA AAAAAGCGTA GAACTGACAC GTAAAATCTT CGCCGATCTC     120

GGTGCATGGC AGATTGCGCA ACTGGCACGC CATCCACAGC GTCCTTATAC CCTGGATTAC     180

GTTCGCCTGG CATTTGATGA ATTTGACGAA CTGGCTGGCG ACCGCGCGTA TGCAGACGAT     240

AAAGCTATCG TCGGTGGTAT CGCCCGTCTC GATGGTCGTC CGGTGATGAT CATTGGTCAT     300

CAAAAAGGTC GTGAAACCAA AGAAAAAATT CGCCGTAACT TTGGTATGCC AGCGCCAGAA     360

GGTTACCGCA AAGCACTGCG TCTGATGCAA ATGGCTGAAC GCTTTAAGAT GCCTATCATC     420

ACCTTTATCG ACACCCCGGG GGCTTATCCT GGCGTGGGCG CAGAAGAGCG TGGTCAGTCT     480

GAAGCCATTG CACGCAACCT GCGTGAAATG TCTCGCCTCG GCGTACCGGT AGTTTGTACG     540

GTTATCGGTG AAGGTGGTTC TGGCGGTGCG CTGGCGATTG GCGTGGGCGA TAAAGTGAAT     600

ATGCTGCAAT ACAGCACCTA TTCCGTTATC TCGCCGGAAG GTTGTGCGTC CATTCTGTGG     660

AAGAGCGCCG ACAAAGCGCC GCTGGCGGCT GAAGCGATGG GTATCATTGC TCCGCGTCTG     720

AAAGAACTGA AACTGATCGA CTCCATCATC CCGGAACCAC TGGGTGGTGC TCACCGTAAC     780

CCGGAAGCGA TGGCGGCATC GTTGAAAGCG CAACTGCTGG CGGATCTGGC CGATCTCGAC     840

GTGTTAAGCA CTGAAGATTT AAAAAATCGT CGTTATCAGC GCCTGATGAG CTACGGTTAC     900

GCGTAATTCG CAAAAGTTCT GAAAAAGGGT CACTTCGGTG GCCCTTTTTT ATCGCCACGG     960

TTTGAGCAGG CTATGATTAA GGAAGGATTT TCCAGGAGGA ACAC ATG AAC ATC ATT     1016
                                                Met Asn Ile Ile
                                                  1

GCC ATT ATG GGA CCG CAT GGC GTC TTT TAT AAA GAT GAG CCC ATC AAA     1064
Ala Ile Met Gly Pro His Gly Val Phe Tyr Lys Asp Glu Pro Ile Lys
  5              10                  15                  20

GAA CTG GAG TCG GCG CTG GTG GCG CAA GGC TTT CAG ATT ATC TGG CCA     1112
Glu Leu Glu Ser Ala Leu Val Ala Gln Gly Phe Gln Ile Ile Trp Pro
              25                  30                  35

CAA AAC AGC GTT GAT TTG CTG AAA TTT ATC GAG CAT AAC CCT CGA ATT     1160
Gln Asn Ser Val Asp Leu Leu Lys Phe Ile Glu His Asn Pro Arg Ile
          40                  45                  50

TGC GGC GTG ATT TTT GAC TGG GAT GAG TAC AGT CTC GAT TTA TGT AGC     1208
Cys Gly Val Ile Phe Asp Trp Asp Glu Tyr Ser Leu Asp Leu Cys Ser
      55                  60                  65

GAT ATC AAT CAG CTT AAT GAA TAT CTC CCG CTT TAT GCC TTC ATC AAC     1256
Asp Ile Asn Gln Leu Asn Glu Tyr Leu Pro Leu Tyr Ala Phe Ile Asn
  70                  75                  80

ACC CAC TCG ACG ATG GAT GTC AGC GTG CAG GAT ATG CGG ATG GCG CTC     1304
Thr His Ser Thr Met Asp Val Ser Val Gln Asp Met Arg Met Ala Leu
 85                  90                  95                 100

TGG TTT TTT GAA TAT GCG CTG GGG CAG GCG GAA GAT ATC GCC ATT CGT     1352
Trp Phe Phe Glu Tyr Ala Leu Gly Gln Ala Glu Asp Ile Ala Ile Arg
             105                 110                 115

ATG CGT CAG TAC ACC GAC GAA TAT CTT GAT AAC ATT ACA CCG CCG TTC     1400
Met Arg Gln Tyr Thr Asp Glu Tyr Leu Asp Asn Ile Thr Pro Pro Phe
```

-continued

```
                            120                                 125                                 130
ACG  AAA  GCC  TTG  TTT  ACC  TAC  GTC  AAA  GAG  CGG  AAG  TAC  ACC  TTT  TGT        1448
Thr  Lys  Ala  Leu  Phe  Thr  Tyr  Val  Lys  Glu  Arg  Lys  Tyr  Thr  Phe  Cys
          135                      140                               145

ACG  CCG  GGG  CAT  ATG  GGC  GGC  ACC  GCA  TAT  CAA  AAA  AGC  CCG  GTT  GGC        1496
Thr  Pro  Gly  His  Met  Gly  Gly  Thr  Ala  Tyr  Gln  Lys  Ser  Pro  Val  Gly
     150                           155                     160

TGT  CTG  TTT  TAT  GAT  TTT  TTC  GGC  GGG  AAT  ACT  CTT  AAG  GCT  GAT  GTC        1544
Cys  Leu  Phe  Tyr  Asp  Phe  Phe  Gly  Gly  Asn  Thr  Leu  Lys  Ala  Asp  Val
165                      170                      175                           180

TCT  ATT  TCG  GTC  ACC  GAG  CTT  GGT  TCG  TTG  CTC  GAC  CAC  ACC  GGG  CCA        1592
Ser  Ile  Ser  Val  Thr  Glu  Leu  Gly  Ser  Leu  Leu  Asp  His  Thr  Gly  Pro
                         185                      190                      195

CAC  CTG  GAA  GCG  GAA  GAG  TAC  ATC  GCG  CGG  ACT  TTT  GGC  GCG  GAA  CAG        1640
His  Leu  Glu  Ala  Glu  Glu  Tyr  Ile  Ala  Arg  Thr  Phe  Gly  Ala  Glu  Gln
               200                      205                      210

AGT  TAT  ATC  GTT  ACC  AAC  GGA  ACA  TCG  ACG  TCG  AAC  AAA  ATT  GTG  GGT        1688
Ser  Tyr  Ile  Val  Thr  Asn  Gly  Thr  Ser  Thr  Ser  Asn  Lys  Ile  Val  Gly
          215                      220                      225

ATG  TAC  GCC  GCG  CCA  TCC  GGC  AGT  ACG  CTG  TTG  ATC  GAC  CGC  AAT  TGT        1736
Met  Tyr  Ala  Ala  Pro  Ser  Gly  Ser  Thr  Leu  Leu  Ile  Asp  Arg  Asn  Cys
     230                           235                          240

CAT  AAA  TCG  CTG  GCG  CAT  CTG  TTG  ATG  ATG  AAC  GAT  GTA  GTG  CCA  GTC        1784
His  Lys  Ser  Leu  Ala  His  Leu  Leu  Met  Met  Asn  Asp  Val  Val  Pro  Val
245                      250                      255                          260

TGG  CTG  AAA  CCG  ACG  CGT  AAT  GCG  TTG  GGG  ATT  CTT  GGT  GGG  ATC  CCG        1832
Trp  Leu  Lys  Pro  Thr  Arg  Asn  Ala  Leu  Gly  Ile  Leu  Gly  Gly  Ile  Pro
                    265                      270                          275

CGC  CGT  GAA  TTT  ACT  CGC  GAC  AGC  ATC  GAA  GAG  AAA  GTC  GCT  GCT  ACC        1880
Arg  Arg  Glu  Phe  Thr  Arg  Asp  Ser  Ile  Glu  Glu  Lys  Val  Ala  Ala  Thr
                    280                      285                          290

ACG  CAA  GCA  CAA  TGG  CCG  GTT  CAT  GCG  GTG  ATC  ACC  AAC  TCC  ACC  TAT        1928
Thr  Gln  Ala  Gln  Trp  Pro  Val  His  Ala  Val  Ile  Thr  Asn  Ser  Thr  Tyr
          295                      300                      305

GAT  GGC  TTG  CTC  TAC  AAC  ACC  GAC  TGG  ATC  AAA  CAG  ACG  CTG  GAT  GTC        1976
Asp  Gly  Leu  Leu  Tyr  Asn  Thr  Asp  Trp  Ile  Lys  Gln  Thr  Leu  Asp  Val
     310                           315                     320

CCG  TCG  ATT  CAC  TTC  GAT  TCT  GCC  TGG  GTG  CCG  TAC  ACC  CAT  TTT  CAT        2024
Pro  Ser  Ile  His  Phe  Asp  Ser  Ala  Trp  Val  Pro  Tyr  Thr  His  Phe  His
325                      330                      335                          340

CCG  ATC  TAC  CAG  GGT  AAA  AGT  GGT  ATG  AGC  GGC  GAG  CGT  GTT  GCG  GGA        2072
Pro  Ile  Tyr  Gln  Gly  Lys  Ser  Gly  Met  Ser  Gly  Glu  Arg  Val  Ala  Gly
                    345                      350                          355

AAA  GTG  ATC  TTC  GAA  ACG  CAA  TCG  ACC  CAC  AAA  ATG  CTG  GCG  GCG  TTA        2120
Lys  Val  Ile  Phe  Glu  Thr  Gln  Ser  Thr  His  Lys  Met  Leu  Ala  Ala  Leu
               360                      365                      370

TCG  CAG  GCT  TCG  CTG  ATC  CAC  ATT  AAA  GGC  GAG  TAT  GAC  GAA  GAG  GCC        2168
Ser  Gln  Ala  Ser  Leu  Ile  His  Ile  Lys  Gly  Glu  Tyr  Asp  Glu  Glu  Ala
          375                      380                      385

TTT  AAC  GAA  GCC  TTT  ATG  ATG  CAT  ACC  ACC  ACC  TCG  CCC  AGT  TAT  CCC        2216
Phe  Asn  Glu  Ala  Phe  Met  Met  His  Thr  Thr  Thr  Ser  Pro  Ser  Tyr  Pro
     390                           395                     400

ATT  GTT  GCT  TCG  GTT  GAG  ACG  GCG  GCG  GCG  ATG  CTG  CGT  GGT  AAT  CCG        2264
Ile  Val  Ala  Ser  Val  Glu  Thr  Ala  Ala  Ala  Met  Leu  Arg  Gly  Asn  Pro
405                      410                      415                          420

GGC  AAA  CGG  CTG  ATT  AAC  CGT  TCA  GTA  GAA  CGA  GCT  CTG  CAT  TTT  CGC        2312
Gly  Lys  Arg  Leu  Ile  Asn  Arg  Ser  Val  Glu  Arg  Ala  Leu  His  Phe  Arg
                    425                      430                          435

AAA  GAG  GTC  CAG  CGG  CTG  CGG  GAA  GAG  TCT  GAC  GGT  TGG  TTT  TTC  GAT        2360
Lys  Glu  Val  Gln  Arg  Leu  Arg  Glu  Glu  Ser  Asp  Gly  Trp  Phe  Phe  Asp
```

|     |     |     |     |     |     |     |     |     |     |     |     |     |     |     |     |      |
|---|---|---|---|---|---|---|---|---|---|---|---|---|---|---|---|---|
|     |     |     |     | 440 |     |     |     |     |     | 445 |     |     |     |     | 450 |      |
| ATC | TGG | CAA | CCG | CCG | CAG | GTG | GAT | GAA | GCC | GAA | TGC | TGG | CCC | GTT | GCG | 2408 |
| Ile | Trp | Gln | Pro | Pro | Gln | Val | Asp | Glu | Ala | Glu | Cys | Trp | Pro | Val | Ala |      |
|     |     | 455 |     |     |     |     | 460 |     |     |     |     | 465 |     |     |     |      |
| CCT | GGC | GAA | CAG | TGG | CAC | GGC | TTT | AAC | GAT | GCG | GAT | GCC | GAT | CAT | ATG | 2456 |
| Pro | Gly | Glu | Gln | Trp | His | Gly | Phe | Asn | Asp | Ala | Asp | Ala | Asp | His | Met |      |
|     | 470 |     |     |     | 475 |     |     |     |     | 480 |     |     |     |     |     |      |
| TTT | CTC | GAT | CCG | GTT | AAA | GTC | ACT | ATT | TTG | ACA | CCG | GGG | ATG | GAC | GAG | 2504 |
| Phe | Leu | Asp | Pro | Val | Lys | Val | Thr | Ile | Leu | Thr | Pro | Gly | Met | Asp | Glu |      |
| 485 |     |     |     |     | 490 |     |     |     |     | 495 |     |     |     |     | 500 |      |
| CAG | GGC | AAT | ATG | AGC | GAG | GAG | GGG | ATC | CCG | GCG | GCG | CTG | GTA | GCA | AAA | 2552 |
| Gln | Gly | Asn | Met | Ser | Glu | Glu | Gly | Ile | Pro | Ala | Ala | Leu | Val | Ala | Lys |      |
|     |     |     |     | 505 |     |     |     |     | 510 |     |     |     |     | 515 |     |      |
| TTC | CTC | GAC | GAA | CGT | GGG | ATC | GTA | GTA | GAG | AAA | ACC | GGC | CCT | TAT | AAC | 2600 |
| Phe | Leu | Asp | Glu | Arg | Gly | Ile | Val | Val | Glu | Lys | Thr | Gly | Pro | Tyr | Asn |      |
|     |     |     | 520 |     |     |     |     | 525 |     |     |     |     | 530 |     |     |      |
| CTG | CTG | TTT | CTC | TTT | AGT | ATT | GGC | ATC | GAT | AAA | ACC | AAA | GCA | ATG | GGA | 2648 |
| Leu | Leu | Phe | Leu | Phe | Ser | Ile | Gly | Ile | Asp | Lys | Thr | Lys | Ala | Met | Gly |      |
|     |     | 535 |     |     |     |     | 540 |     |     |     |     | 545 |     |     |     |      |
| TTA | TTG | CGT | GGG | TTG | ACG | GAA | TTC | AAA | CGC | TCT | TAC | GAT | CTC | AAC | CTG | 2696 |
| Leu | Leu | Arg | Gly | Leu | Thr | Glu | Phe | Lys | Arg | Ser | Tyr | Asp | Leu | Asn | Leu |      |
| 550 |     |     |     |     | 555 |     |     |     |     | 560 |     |     |     |     |     |      |
| CGG | ATC | AAA | AAT | ATG | CTA | CCC | GAT | CTC | TAT | GCA | GAA | GAT | CCC | GAT | TTC | 2744 |
| Arg | Ile | Lys | Asn | Met | Leu | Pro | Asp | Leu | Tyr | Ala | Glu | Asp | Pro | Asp | Phe |      |
| 565 |     |     |     |     | 570 |     |     |     |     | 575 |     |     |     |     | 580 |      |
| TAC | CGC | AAT | ATG | CGT | ATT | CAG | GAT | CTG | GCA | CAA | GGG | ATC | CAT | AAG | CTG | 2792 |
| Tyr | Arg | Asn | Met | Arg | Ile | Gln | Asp | Leu | Ala | Gln | Gly | Ile | His | Lys | Leu |      |
|     |     |     |     | 585 |     |     |     |     | 590 |     |     |     |     | 595 |     |      |
| ATT | CGT | AAA | CAC | GAT | CTT | CCC | GGT | TTG | ATG | TTG | CGG | GCA | TTC | GAT | ACT | 2840 |
| Ile | Arg | Lys | His | Asp | Leu | Pro | Gly | Leu | Met | Leu | Arg | Ala | Phe | Asp | Thr |      |
|     |     |     | 600 |     |     |     |     | 605 |     |     |     |     | 610 |     |     |      |
| TTG | CCG | GAG | ATG | ATC | ATG | ACG | CCA | CAT | CAG | GCA | TGG | CAA | CGA | CAA | ATT | 2888 |
| Leu | Pro | Glu | Met | Ile | Met | Thr | Pro | His | Gln | Ala | Trp | Gln | Arg | Gln | Ile |      |
|     |     | 615 |     |     |     |     | 620 |     |     |     |     | 625 |     |     |     |      |
| AAA | GGC | GAA | GTA | GAA | ACC | ATT | GCG | CTG | GAA | CAA | CTG | GTC | GGT | AGA | GTA | 2936 |
| Lys | Gly | Glu | Val | Glu | Thr | Ile | Ala | Leu | Glu | Gln | Leu | Val | Gly | Arg | Val |      |
|     | 630 |     |     |     |     | 635 |     |     |     |     | 640 |     |     |     |     |      |
| TCG | GCA | AAT | ATG | ATC | CTG | CCT | TAT | CCA | CCG | GGC | GTA | CCG | CTG | TTG | ATG | 2984 |
| Ser | Ala | Asn | Met | Ile | Leu | Pro | Tyr | Pro | Pro | Gly | Val | Pro | Leu | Leu | Met |      |
| 645 |     |     |     |     | 650 |     |     |     |     | 655 |     |     |     |     | 660 |      |
| CCT | GGA | GAA | ATG | CTG | ACC | AAA | GAG | AGC | CGC | ACA | GTA | CTC | GAT | TTT | CTA | 3032 |
| Pro | Gly | Glu | Met | Leu | Thr | Lys | Glu | Ser | Arg | Thr | Val | Leu | Asp | Phe | Leu |      |
|     |     |     |     | 665 |     |     |     |     | 670 |     |     |     |     | 675 |     |      |
| CTG | ATG | CTT | TGT | TCC | GTC | GGG | CAA | CAT | TAC | CCC | GGT | TTT | GAA | ACG | GAT | 3080 |
| Leu | Met | Leu | Cys | Ser | Val | Gly | Gln | His | Tyr | Pro | Gly | Phe | Glu | Thr | Asp |      |
|     |     |     | 680 |     |     |     |     | 685 |     |     |     |     | 690 |     |     |      |
| ATT | CAC | GGC | GCG | AAA | CAG | GAC | GAA | GAC | GGC | GTT | TAC | CGC | GTA | CGA | GTC | 3128 |
| Ile | His | Gly | Ala | Lys | Gln | Asp | Glu | Asp | Gly | Val | Tyr | Arg | Val | Arg | Val |      |
|     |     | 695 |     |     |     |     | 700 |     |     |     |     | 705 |     |     |     |      |
| CTA | AAA | ATG | GCG | GGA | TAACTTGCCA | | GAGCGGCTTC | | CGGGCGAGTA | | ACGTTCTGTT | | | | | 3183 |
| Leu | Lys | Met | Ala | Gly |     |     |     |     |     |     |     |     |     |     |     |      |
|     |     | 710 |     |     |     |     |     |     |     |     |     |     |     |     |     |      |

( 2 ) INFORMATION FOR SEQ ID NO:4:

( i ) SEQUENCE CHARACTERISTICS:
        ( A ) LENGTH: 713 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Asn Ile Ile Ala Ile Met Gly Pro His Gly Val Phe Tyr Lys Asp
 1               5                  10                  15
Glu Pro Ile Lys Glu Leu Glu Ser Ala Leu Val Ala Gln Gly Phe Gln
                20                  25                  30
Ile Ile Trp Pro Gln Asn Ser Val Asp Leu Leu Lys Phe Ile Glu His
            35                  40                  45
Asn Pro Arg Ile Cys Gly Val Ile Phe Asp Trp Asp Glu Tyr Ser Leu
        50                  55                  60
Asp Leu Cys Ser Asp Ile Asn Gln Leu Asn Glu Tyr Leu Pro Leu Tyr
 65                 70                  75                  80
Ala Phe Ile Asn Thr His Ser Thr Met Asp Val Ser Val Gln Asp Met
                85                  90                  95
Arg Met Ala Leu Trp Phe Phe Glu Tyr Ala Leu Gly Gln Ala Glu Asp
                100                 105                 110
Ile Ala Ile Arg Met Arg Gln Tyr Thr Asp Glu Tyr Leu Asp Asn Ile
            115                 120                 125
Thr Pro Pro Phe Thr Lys Ala Leu Phe Thr Tyr Val Lys Glu Arg Lys
        130                 135                 140
Tyr Thr Phe Cys Thr Pro Gly His Met Gly Gly Thr Ala Tyr Gln Lys
 145                150                 155                 160
Ser Pro Val Gly Cys Leu Phe Tyr Asp Phe Phe Gly Gly Asn Thr Leu
                165                 170                 175
Lys Ala Asp Val Ser Ile Ser Val Thr Glu Leu Gly Ser Leu Leu Asp
                180                 185                 190
His Thr Gly Pro His Leu Glu Ala Glu Glu Tyr Ile Ala Arg Thr Phe
            195                 200                 205
Gly Ala Glu Gln Ser Tyr Ile Val Thr Asn Gly Thr Ser Thr Ser Asn
        210                 215                 220
Lys Ile Val Gly Met Tyr Ala Ala Pro Ser Gly Ser Thr Leu Leu Ile
 225                230                 235                 240
Asp Arg Asn Cys His Lys Ser Leu Ala His Leu Leu Met Met Asn Asp
                245                 250                 255
Val Val Pro Val Trp Leu Lys Pro Thr Arg Asn Ala Leu Gly Ile Leu
                260                 265                 270
Gly Gly Ile Pro Arg Arg Glu Phe Thr Arg Asp Ser Ile Glu Glu Lys
            275                 280                 285
Val Ala Ala Thr Thr Gln Ala Gln Trp Pro Val His Ala Val Ile Thr
        290                 295                 300
Asn Ser Thr Tyr Asp Gly Leu Leu Tyr Asn Thr Asp Trp Ile Lys Gln
 305                310                 315                 320
Thr Leu Asp Val Pro Ser Ile His Phe Asp Ser Ala Trp Val Pro Tyr
                325                 330                 335
Thr His Phe His Pro Ile Tyr Gln Gly Lys Ser Gly Met Ser Gly Glu
                340                 345                 350
Arg Val Ala Gly Lys Val Ile Phe Glu Thr Gln Ser Thr His Lys Met
            355                 360                 365
Leu Ala Ala Leu Ser Gln Ala Ser Leu Ile His Ile Lys Gly Glu Tyr
        370                 375                 380
Asp Glu Glu Ala Phe Asn Glu Ala Phe Met Met His Thr Thr Thr Ser
 385                390                 395                 400
Pro Ser Tyr Pro Ile Val Ala Ser Val Glu Thr Ala Ala Ala Met Leu
                405                 410                 415
```

| | | | | | | | | | | | | | | |
|---|---|---|---|---|---|---|---|---|---|---|---|---|---|---|
| Arg | Gly | Asn | Pro 420 | Gly | Lys | Arg | Leu | Ile 425 | Asn | Arg | Ser | Val | Glu 430 | Arg | Ala |
| Leu | His | Phe 435 | Arg | Lys | Glu | Val 440 | Gln | Arg | Leu | Arg | Glu 445 | Glu | Ser | Asp | Gly |
| Trp | Phe 450 | Phe | Asp | Ile | Trp 455 | Gln | Pro | Pro | Gln | Val 460 | Asp | Glu | Ala | Glu | Cys |
| Trp 465 | Pro | Val | Ala | Pro 470 | Gly | Glu | Gln | Trp | His 475 | Gly | Phe | Asn | Asp | Ala | Asp 480 |
| Ala | Asp | His | Met | Phe 485 | Leu | Asp | Pro | Val | Lys 490 | Val | Thr | Ile | Leu | Thr 495 | Pro |
| Gly | Met | Asp | Glu 500 | Gln | Gly | Asn | Met | Ser 505 | Glu | Glu | Gly | Ile | Pro 510 | Ala | Ala |
| Leu | Val | Ala 515 | Lys | Phe | Leu | Asp | Glu 520 | Arg | Gly | Ile | Val | Val 525 | Glu | Lys | Thr |
| Gly | Pro 530 | Tyr | Asn | Leu | Leu | Phe 535 | Leu | Phe | Ser | Ile | Gly 540 | Ile | Asp | Lys | Thr |
| Lys 545 | Ala | Met | Gly | Leu | Leu 550 | Arg | Gly | Leu | Thr | Glu 555 | Phe | Lys | Arg | Ser | Tyr 560 |
| Asp | Leu | Asn | Leu | Arg 565 | Ile | Lys | Asn | Met | Leu 570 | Pro | Asp | Leu | Tyr | Ala 575 | Glu |
| Asp | Pro | Asp | Phe 580 | Tyr | Arg | Asn | Met | Arg 585 | Ile | Gln | Asp | Leu | Ala 590 | Gln | Gly |
| Ile | His | Lys 595 | Leu | Ile | Arg | Lys | His 600 | Asp | Leu | Pro | Gly | Leu 605 | Met | Leu | Arg |
| Ala | Phe 610 | Asp | Thr | Leu | Pro | Glu 615 | Met | Ile | Met | Thr | Pro 620 | His | Gln | Ala | Trp |
| Gln 625 | Arg | Gln | Ile | Lys | Gly 630 | Glu | Val | Glu | Thr | Ile 635 | Ala | Leu | Glu | Gln | Leu 640 |
| Val | Gly | Arg | Val | Ser 645 | Ala | Asn | Met | Ile | Leu 650 | Pro | Tyr | Pro | Pro | Gly 655 | Val |
| Pro | Leu | Leu | Met 660 | Pro | Gly | Glu | Met | Leu 665 | Thr | Lys | Glu | Ser | Arg 670 | Thr | Val |
| Leu | Asp | Phe 675 | Leu | Leu | Met | Leu | Cys 680 | Ser | Val | Gly | Gln | His 685 | Tyr | Pro | Gly |
| Phe | Glu 690 | Thr | Asp | Ile | His | Gly 695 | Ala | Lys | Gln | Asp | Glu 700 | Asp | Gly | Val | Tyr |
| Arg 705 | Val | Arg | Val | Leu | Lys 710 | Met | Ala | Gly | | | | | | | |

( 2 ) INFORMATION FOR SEQ ID NO:5:

( i ) SEQUENCE CHARACTERISTICS:
        ( A ) LENGTH: 2145 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Escherichia coli
        ( B ) STRAIN: CS520

( i x ) FEATURE:
        ( A ) NAME/KEY: CDS
        ( B ) LOCATION: 1..2145

( x i ) SEQUENCE DESCRIPTION: SEQ ID NO:5:

| | | | | | | | | | | | | | | | | |
|---|---|---|---|---|---|---|---|---|---|---|---|---|---|---|---|---|
| ATG | AAC | GTT | ATT | GCA | ATA | TTG | AAT | CAC | ATG | GGG | GTT | TAT | TTT | AAA | GAA | 48 |
| Met | Asn | Val | Ile | Ala | Ile | Leu | Asn | His | Met | Gly | Val | Tyr | Phe | Lys | Glu | |
| 1 | | | | 5 | | | | | 10 | | | | | 15 | | |
| GAA | CCC | ATC | CGT | GAA | CTT | CAT | CGC | GCG | CTT | GAA | CGT | CTG | AAC | TTC | CAG | 96 |
| Glu | Pro | Ile | Arg | Glu | Leu | His | Arg | Ala | Leu | Glu | Arg | Leu | Asn | Phe | Gln | |
| | | | 20 | | | | | 25 | | | | | 30 | | | |
| ATT | GTT | TAC | CCG | AAC | GAC | CGT | GAC | GAC | TTA | TTA | AAA | CTG | ATC | GAA | AAC | 144 |
| Ile | Val | Tyr | Pro | Asn | Asp | Arg | Asp | Asp | Leu | Leu | Lys | Leu | Ile | Glu | Asn | |
| | | 35 | | | | | 40 | | | | | 45 | | | | |
| AAT | GCG | CGT | CTG | TGC | GGC | GTT | ATT | TTT | GAC | TGG | GAT | AAA | TAT | AAT | CTC | 192 |
| Asn | Ala | Arg | Leu | Cys | Gly | Val | Ile | Phe | Asp | Trp | Asp | Lys | Tyr | Asn | Leu | |
| | 50 | | | | | 55 | | | | | 60 | | | | | |
| GAG | CTG | TGC | GAA | GAA | ATT | AGC | AAA | ATG | AAC | GAG | AAC | CTG | CCG | TTG | TAC | 240 |
| Glu | Leu | Cys | Glu | Glu | Ile | Ser | Lys | Met | Asn | Glu | Asn | Leu | Pro | Leu | Tyr | |
| 65 | | | | | 70 | | | | | 75 | | | | | 80 | |
| GCG | TTC | GCT | AAT | ACG | TAT | TCC | ACT | CTC | GAT | GTA | AGC | CTG | AAT | GAC | CTG | 288 |
| Ala | Phe | Ala | Asn | Thr | Tyr | Ser | Thr | Leu | Asp | Val | Ser | Leu | Asn | Asp | Leu | |
| | | | | 85 | | | | | 90 | | | | | 95 | | |
| CGT | TTA | CAG | ATT | AGC | TTC | TTT | GAA | TAT | GCG | CTG | GGT | GCT | GCT | GAA | GAT | 336 |
| Arg | Leu | Gln | Ile | Ser | Phe | Phe | Glu | Tyr | Ala | Leu | Gly | Ala | Ala | Glu | Asp | |
| | | | 100 | | | | | 105 | | | | | 110 | | | |
| CTG | CCT | CCG | CTG | ACT | AAA | GCA | CTG | TTT | AAA | TAT | GTT | CGT | GAA | GGT | AAA | 384 |
| Leu | Pro | Pro | Leu | Thr | Lys | Ala | Leu | Phe | Lys | Tyr | Val | Arg | Glu | Gly | Lys | |
| | | 115 | | | | | 120 | | | | | 125 | | | | |
| ATT | GCT | AAT | AAG | ATC | AAG | CAG | ACC | ACT | GAC | GAA | TAT | ATC | AAC | ACT | ATT | 432 |
| Ile | Ala | Asn | Lys | Ile | Lys | Gln | Thr | Thr | Asp | Glu | Tyr | Ile | Asn | Thr | Ile | |
| | 130 | | | | | 135 | | | | | 140 | | | | | |
| TAT | ACT | TTC | TGT | ACT | CCT | GGT | CAC | ATG | GGC | GGT | ACT | GCA | TTC | CAG | AAA | 480 |
| Tyr | Thr | Phe | Cys | Thr | Pro | Gly | His | Met | Gly | Gly | Thr | Ala | Phe | Gln | Lys | |
| 145 | | | | | 150 | | | | | 155 | | | | | 160 | |
| AGC | CCG | GTA | GGT | AGC | CTG | TTC | TAT | GAT | TTC | TTT | GGT | CCG | AAT | ACC | ATG | 528 |
| Ser | Pro | Val | Gly | Ser | Leu | Phe | Tyr | Asp | Phe | Phe | Gly | Pro | Asn | Thr | Met | |
| | | | | 165 | | | | | 170 | | | | | 175 | | |
| AAA | TCT | GAT | ATT | TCC | ATT | TCA | GTA | TCT | GAA | CTG | GGT | TCT | CTG | CTG | GAT | 576 |
| Lys | Ser | Asp | Ile | Ser | Ile | Ser | Val | Ser | Glu | Leu | Gly | Ser | Leu | Leu | Asp | |
| | | | 180 | | | | | 185 | | | | | 190 | | | |
| CAC | AGT | GGT | CCA | CAC | AAA | GAA | GCA | GAA | CAG | TAT | ATC | GCT | CGC | GTC | TTT | 624 |
| His | Ser | Gly | Pro | His | Lys | Glu | Ala | Glu | Gln | Tyr | Ile | Ala | Arg | Val | Phe | |
| | | 195 | | | | | 200 | | | | | 205 | | | | |
| AAC | GCA | GAC | CGC | AGC | TAC | ATG | GTG | ACC | AAC | GGT | ACT | TCC | ACT | GCG | AAC | 672 |
| Asn | Ala | Asp | Arg | Ser | Tyr | Met | Val | Thr | Asn | Gly | Thr | Ser | Thr | Ala | Asn | |
| | 210 | | | | | 215 | | | | | 220 | | | | | |
| AAA | ATT | GTT | GGT | ATG | TAC | TCT | GCT | CCA | GCA | GGC | AGC | ACC | ATT | CTG | ATT | 720 |
| Lys | Ile | Val | Gly | Met | Tyr | Ser | Ala | Pro | Ala | Gly | Ser | Thr | Ile | Leu | Ile | |
| 225 | | | | | 230 | | | | | 235 | | | | | 240 | |
| GAC | CGT | AAC | TGC | CAC | AAA | TCG | CTG | ACC | CAC | CTG | ATG | ATG | ATG | AGC | GAT | 768 |
| Asp | Arg | Asn | Cys | His | Lys | Ser | Leu | Thr | His | Leu | Met | Met | Met | Ser | Asp | |
| | | | | 245 | | | | | 250 | | | | | 255 | | |
| GTT | ACG | CCA | ATC | TAT | TTC | CGC | CCG | ACC | CGT | AAC | GCT | TAC | GGT | ATT | CTT | 816 |
| Val | Thr | Pro | Ile | Tyr | Phe | Arg | Pro | Thr | Arg | Asn | Ala | Tyr | Gly | Ile | Leu | |
| | | | 260 | | | | | 265 | | | | | 270 | | | |
| GGT | GGT | ATC | CCA | CAG | AGT | GAA | TTC | CAG | CAC | GCT | ACC | ATT | GCT | AAG | CGC | 864 |
| Gly | Gly | Ile | Pro | Gln | Ser | Glu | Phe | Gln | His | Ala | Thr | Ile | Ala | Lys | Arg | |
| | | 275 | | | | | 280 | | | | | 285 | | | | |
| GTG | AAA | GAA | ACA | CCA | AAC | GCA | ACC | TGG | CCG | GTA | CAT | GCT | GTA | ATT | ACC | 912 |
| Val | Lys | Glu | Thr | Pro | Asn | Ala | Thr | Trp | Pro | Val | His | Ala | Val | Ile | Thr | |
| | 290 | | | | | 295 | | | | | 300 | | | | | |
| AAC | TCT | ACC | TAT | GAT | GGT | CTG | CTG | TAC | AAC | ACC | GAC | TTC | ATC | AAG | AAA | 960 |
| Asn | Ser | Thr | Tyr | Asp | Gly | Leu | Leu | Tyr | Asn | Thr | Asp | Phe | Ile | Lys | Lys | |

|  |  |  |  |  |  |  |  |  |  |  |  |  |  |  |  |
|---|---|---|---|---|---|---|---|---|---|---|---|---|---|---|---|
| 305 |  |  |  |  | 310 |  |  |  |  | 315 |  |  |  |  | 320 |

```
ACA CTG GAT GTG AAA TCC ATC CAC TTT GAC TCC GCG TGG GTG CCT TAC      1008
Thr Leu Asp Val Lys Ser Ile His Phe Asp Ser Ala Trp Val Pro Tyr
            325                 330                 335

ACC AAC TTC TCA CCG ATT TAC GAA GGT AAA TGC GGT ATG AGC GGT GGC      1056
Thr Asn Phe Ser Pro Ile Tyr Glu Gly Lys Cys Gly Met Ser Gly Gly
                340                 345                 350

CGT GTA GAA GGG AAA GTG ATT TAC GAA ACC CAG TCC ACT CAC AAA CTG      1104
Arg Val Glu Gly Lys Val Ile Tyr Glu Thr Gln Ser Thr His Lys Leu
                355                 360                 365

CTG GCG GCG TTC TCT CAG GCT TCC ATG ATC CAC GTT AAA GGT GAC GTA      1152
Leu Ala Ala Phe Ser Gln Ala Ser Met Ile His Val Lys Gly Asp Val
            370                 375                 380

AAC GAA GAA ACC TTT AAC GAA GCC TAC ATG ATG CAC ACC ACC ACT TCT      1200
Asn Glu Glu Thr Phe Asn Glu Ala Tyr Met Met His Thr Thr Thr Ser
385                 390                 395                 400

CCG CAC TAC GGT ATC GTG GCG TCC ACT GAA ACC GCT GCG GCG ATG ATG      1248
Pro His Tyr Gly Ile Val Ala Ser Thr Glu Thr Ala Ala Ala Met Met
                405                 410                 415

AAA GGC AAT GCA GGT AAG CGT CTG ATC AAC GGT TCT ATT GAA CGT GCG      1296
Lys Gly Asn Ala Gly Lys Arg Leu Ile Asn Gly Ser Ile Glu Arg Ala
                420                 425                 430

ATC AAA TTC CGT AAA GAG ATC AAA CGT CTG AGA ACG GAA TCT GAT GGC      1344
Ile Lys Phe Arg Lys Glu Ile Lys Arg Leu Arg Thr Glu Ser Asp Gly
            435                 440                 445

TGG TTC TTT GAT GTA TGG CAG CCG GAT CAT ATC GAT ACG ACT GAA TGC      1392
Trp Phe Phe Asp Val Trp Gln Pro Asp His Ile Asp Thr Thr Glu Cys
            450                 455                 460

TGG CCG CTG CGT TCT GAC AGC ACC TGG CAC GGC TTC AAA AAC ATC GAT      1440
Trp Pro Leu Arg Ser Asp Ser Thr Trp His Gly Phe Lys Asn Ile Asp
465                 470                 475                 480

AAC GAG CAC ATG TAT CTT GAC CCG ATC AAA GTC ACC CTG CTG ACT CCG      1488
Asn Glu His Met Tyr Leu Asp Pro Ile Lys Val Thr Leu Leu Thr Pro
                485                 490                 495

GGG ATG GAA AAA GAC GGC ACC ATG AGC GAC TTT GGT ATT CCG GCC AGC      1536
Gly Met Glu Lys Asp Gly Thr Met Ser Asp Phe Gly Ile Pro Ala Ser
                500                 505                 510

ATC GTG GCG AAA TAC CTC GAC GAA CAT GGC ATC GTT GTT GAG AAA ACC      1584
Ile Val Ala Lys Tyr Leu Asp Glu His Gly Ile Val Val Glu Lys Thr
            515                 520                 525

GGT CCG TAT AAC CTG CTG TTC CTG TTC AGC ATC GGT ATC GAT AAG ACC      1632
Gly Pro Tyr Asn Leu Leu Phe Leu Phe Ser Ile Gly Ile Asp Lys Thr
            530                 535                 540

AAA GCA CTG AGC CTG CTG CGT GCT CTG ACT GAC TTT AAA CGT GCG TTC      1680
Lys Ala Leu Ser Leu Leu Arg Ala Leu Thr Asp Phe Lys Arg Ala Phe
545                 550                 555                 560

GAC CTG AAC CTG CGT GTG AAA AAC ATG CTG CCG TCT CTG TAT CGT GAA      1728
Asp Leu Asn Leu Arg Val Lys Asn Met Leu Pro Ser Leu Tyr Arg Glu
                565                 570                 575

GAT CCT GAA TTC TAT GAA AAC ATG CGT ATT CAG GAA CTG GCT CAG AAT      1776
Asp Pro Glu Phe Tyr Glu Asn Met Arg Ile Gln Glu Leu Ala Gln Asn
                580                 585                 590

ATC CAC AAA CTG ATT GTT CAC CAC AAT CTG CCG GAT CTG ATG TAT CGC      1824
Ile His Lys Leu Ile Val His His Asn Leu Pro Asp Leu Met Tyr Arg
            595                 600                 605

GCA TTT GAA GTG CTG CCG ACG ATG GTA ATG ACT CCG TAT GCT GCA TTC      1872
Ala Phe Glu Val Leu Pro Thr Met Val Met Thr Pro Tyr Ala Ala Phe
            610                 615                 620

CAG AAA GAG CTG CAC GGT ATG ACC GAA GAA GTT TAC CTC GAC GAA ATG      1920
Gln Lys Glu Leu His Gly Met Thr Glu Glu Val Tyr Leu Asp Glu Met
```

|   |   |   |   |   |   |   |   |   |   |   |   |   |   |   |   |   |
|---|---|---|---|---|---|---|---|---|---|---|---|---|---|---|---|---|
| 625 | | | | | 630 | | | | | 635 | | | | | 640 | |
| GTA | GGT | CGT | ATT | AAC | GCC | AAT | ATG | ATC | CTT | CCG | TAC | CCG | CCG | GGA | GTT | 1968 |
| Val | Gly | Arg | Ile | Asn | Ala | Asn | Met | Ile | Leu | Pro | Tyr | Pro | Pro | Gly | Val | |
| | | | | 645 | | | | | 650 | | | | | 655 | | |
| CCT | CTG | GTA | ATG | CCG | GGT | GAA | ATG | ATC | ACC | GAA | GAA | AGC | CGT | CCG | GTT | 2016 |
| Pro | Leu | Val | Met | Pro | Gly | Glu | Met | Ile | Thr | Glu | Glu | Ser | Arg | Pro | Val | |
| | | | 660 | | | | | 665 | | | | | 670 | | | |
| CTG | GAG | TTC | CTG | CAG | ATG | CTG | TGT | GAA | ATC | GGC | GCT | CAC | TAT | CCG | GGC | 2064 |
| Leu | Glu | Phe | Leu | Gln | Met | Leu | Cys | Glu | Ile | Gly | Ala | His | Tyr | Pro | Gly | |
| | | 675 | | | | | 680 | | | | | 685 | | | | |
| TTT | GAA | ACC | GAT | ATT | CAC | GGT | GCA | TAC | CGT | CAG | GCT | GAT | GGC | CGC | TAT | 2112 |
| Phe | Glu | Thr | Asp | Ile | His | Gly | Ala | Tyr | Arg | Gln | Ala | Asp | Gly | Arg | Tyr | |
| | 690 | | | | | 695 | | | | | 700 | | | | | |
| ACC | GTT | AAG | GTA | TTG | AAA | GAA | GAA | AGC | AAA | AAA | | | | | | 2145 |
| Thr | Val | Lys | Val | Leu | Lys | Glu | Glu | Ser | Lys | Lys | | | | | | |
| 705 | | | | 710 | | | | | 715 | | | | | | | |

( 2 ) INFORMATION FOR SEQ ID NO:6:

( i ) SEQUENCE CHARACTERISTICS:
        ( A ) LENGTH: 715 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

|   |   |   |   |   |   |   |   |   |   |   |   |   |   |   |
|---|---|---|---|---|---|---|---|---|---|---|---|---|---|---|
| Met | Asn | Val | Ile | Ala | Ile | Leu | Asn | His | Met | Gly | Val | Tyr | Phe | Lys | Glu |
| 1 | | | | 5 | | | | | 10 | | | | | 15 |
| Glu | Pro | Ile | Arg | Glu | Leu | His | Arg | Ala | Leu | Glu | Arg | Leu | Asn | Phe | Gln |
| | | | 20 | | | | 25 | | | | | 30 | | |
| Ile | Val | Tyr | Pro | Asn | Asp | Arg | Asp | Leu | Leu | Lys | Leu | Ile | Glu | Asn |
| | | 35 | | | | 40 | | | | 45 | | | |
| Asn | Ala | Arg | Leu | Cys | Gly | Val | Ile | Phe | Asp | Trp | Asp | Lys | Tyr | Asn | Leu |
| | 50 | | | | 55 | | | | 60 | | | | | |
| Glu | Leu | Cys | Glu | Glu | Ile | Ser | Lys | Met | Asn | Glu | Asn | Leu | Pro | Leu | Tyr |
| 65 | | | | 70 | | | | 75 | | | | | 80 |
| Ala | Phe | Ala | Asn | Thr | Tyr | Ser | Thr | Leu | Asp | Val | Ser | Leu | Asn | Asp | Leu |
| | | | 85 | | | | 90 | | | | 95 |
| Arg | Leu | Gln | Ile | Ser | Phe | Phe | Glu | Tyr | Ala | Leu | Gly | Ala | Ala | Glu | Asp |
| | | | 100 | | | | 105 | | | | 110 |
| Leu | Pro | Pro | Leu | Thr | Lys | Ala | Leu | Phe | Lys | Tyr | Val | Arg | Glu | Gly | Lys |
| | | 115 | | | | 120 | | | | 125 |
| Ile | Ala | Asn | Lys | Ile | Lys | Gln | Thr | Thr | Asp | Glu | Tyr | Ile | Asn | Thr | Ile |
| | 130 | | | | 135 | | | | 140 |
| Tyr | Thr | Phe | Cys | Thr | Pro | Gly | His | Met | Gly | Gly | Thr | Ala | Phe | Gln | Lys |
| 145 | | | | 150 | | | | 155 | | | | | 160 |
| Ser | Pro | Val | Gly | Ser | Leu | Phe | Tyr | Asp | Phe | Phe | Gly | Pro | Asn | Thr | Met |
| | | | 165 | | | | 170 | | | | 175 |
| Lys | Ser | Asp | Ile | Ser | Ile | Ser | Val | Ser | Glu | Leu | Gly | Ser | Leu | Leu | Asp |
| | | | 180 | | | | 185 | | | | 190 |
| His | Ser | Gly | Pro | His | Lys | Glu | Ala | Glu | Gln | Tyr | Ile | Ala | Arg | Val | Phe |
| | | 195 | | | | 200 | | | | 205 |
| Asn | Ala | Asp | Arg | Ser | Tyr | Met | Val | Thr | Asn | Gly | Thr | Ser | Thr | Ala | Asn |
| | 210 | | | | 215 | | | | 220 |
| Lys | Ile | Val | Gly | Met | Tyr | Ser | Ala | Pro | Ala | Gly | Ser | Thr | Ile | Leu | Ile |
| 225 | | | | 230 | | | | 235 | | | | | 240 |
| Asp | Arg | Asn | Cys | His | Lys | Ser | Leu | Thr | His | Leu | Met | Met | Met | Ser | Asp |

-continued

```
                         245                          250                          255
Val  Thr  Pro  Ile  Tyr  Phe  Arg  Pro  Thr  Arg  Asn  Ala  Tyr  Gly  Ile  Leu
               260                     265                     270

Gly  Gly  Ile  Pro  Gln  Ser  Glu  Phe  Gln  His  Ala  Thr  Ile  Ala  Lys  Arg
               275                     280                     285

Val  Lys  Glu  Thr  Pro  Asn  Ala  Thr  Trp  Pro  Val  His  Ala  Val  Ile  Thr
     290                     295                     300

Asn  Ser  Thr  Tyr  Asp  Gly  Leu  Leu  Tyr  Asn  Thr  Asp  Phe  Ile  Lys  Lys
305                          310                     315                     320

Thr  Leu  Asp  Val  Lys  Ser  Ile  His  Phe  Asp  Ser  Ala  Trp  Val  Pro  Tyr
                    325                     330                     335

Thr  Asn  Phe  Ser  Pro  Ile  Tyr  Glu  Gly  Lys  Cys  Gly  Met  Ser  Gly  Gly
               340                     345                     350

Arg  Val  Glu  Gly  Lys  Val  Ile  Tyr  Glu  Thr  Gln  Ser  Thr  His  Lys  Leu
               355                     360                     365

Leu  Ala  Ala  Phe  Ser  Gln  Ala  Ser  Met  Ile  His  Val  Lys  Gly  Asp  Val
          370                     375                     380

Asn  Glu  Glu  Thr  Phe  Asn  Glu  Ala  Tyr  Met  Met  His  Thr  Thr  Thr  Ser
385                          390                     395                     400

Pro  His  Tyr  Gly  Ile  Val  Ala  Ser  Thr  Glu  Thr  Ala  Ala  Ala  Met  Met
                    405                     410                     415

Lys  Gly  Asn  Ala  Gly  Lys  Arg  Leu  Ile  Asn  Gly  Ser  Ile  Glu  Arg  Ala
               420                     425                     430

Ile  Lys  Phe  Arg  Lys  Glu  Ile  Lys  Arg  Leu  Arg  Thr  Glu  Ser  Asp  Gly
          435                     440                     445

Trp  Phe  Phe  Asp  Val  Trp  Gln  Pro  Asp  His  Ile  Asp  Thr  Thr  Glu  Cys
     450                     455                     460

Trp  Pro  Leu  Arg  Ser  Asp  Ser  Thr  Trp  His  Gly  Phe  Lys  Asn  Ile  Asp
465                     470                     475                          480

Asn  Glu  His  Met  Tyr  Leu  Asp  Pro  Ile  Lys  Val  Thr  Leu  Leu  Thr  Pro
                    485                     490                     495

Gly  Met  Glu  Lys  Asp  Gly  Thr  Met  Ser  Asp  Phe  Gly  Ile  Pro  Ala  Ser
               500                     505                     510

Ile  Val  Ala  Lys  Tyr  Leu  Asp  Glu  His  Gly  Ile  Val  Val  Glu  Lys  Thr
          515                     520                     525

Gly  Pro  Tyr  Asn  Leu  Leu  Phe  Leu  Phe  Ser  Ile  Gly  Ile  Asp  Lys  Thr
     530                     535                     540

Lys  Ala  Leu  Ser  Leu  Leu  Arg  Ala  Leu  Thr  Asp  Phe  Lys  Arg  Ala  Phe
545                     550                     555                          560

Asp  Leu  Asn  Leu  Arg  Val  Lys  Asn  Met  Leu  Pro  Ser  Leu  Tyr  Arg  Glu
               565                     570                     575

Asp  Pro  Glu  Phe  Tyr  Glu  Asn  Met  Arg  Ile  Gln  Glu  Leu  Ala  Gln  Asn
               580                     585                     590

Ile  His  Lys  Leu  Ile  Val  His  His  Asn  Leu  Pro  Asp  Leu  Met  Tyr  Arg
          595                     600                     605

Ala  Phe  Glu  Val  Leu  Pro  Thr  Met  Val  Met  Thr  Pro  Tyr  Ala  Ala  Phe
     610                     615                     620

Gln  Lys  Glu  Leu  His  Gly  Met  Thr  Glu  Glu  Val  Tyr  Leu  Asp  Glu  Met
625                     630                     635                          640

Val  Gly  Arg  Ile  Asn  Ala  Asn  Met  Ile  Leu  Pro  Tyr  Pro  Pro  Gly  Val
                    645                     650                     655

Pro  Leu  Val  Met  Pro  Gly  Glu  Met  Ile  Thr  Glu  Glu  Ser  Arg  Pro  Val
               660                     665                     670
```

-continued

| Leu | Glu | Phe 675 | Leu | Gln | Met | Leu | Cys 680 | Glu | Ile | Gly | Ala | His 685 | Tyr | Pro | Gly |
| Phe | Glu 690 | Thr | Asp | Ile | His | Gly 695 | Ala | Tyr | Arg | Gln | Ala | Asp 700 | Gly | Arg | Tyr |
| Thr 705 | Val | Lys | Val | Leu | Lys 710 | Glu | Glu | Ser | Lys | Lys 715 | | | | | |